US012727945B2

(12) United States Patent
Quesson et al.

(10) Patent No.: US 12,727,945 B2
(45) Date of Patent: Sep. 8, 2026

(54) HEAT TREATMENT ASSEMBLY

(71) Applicants: Universite de Bordeaux, Bordeaux (FR); INSERM (Institut National de la Santé et de la Recherche Medicale), Paris (FR); Fondation Bordeaux Universite, Bourdeaux (FR)

(72) Inventors: Bruno Quesson, Cestas (FR); Valéry Ozenne, Talence (FR); Pierre Bour, Marcheprime (FR)

(73) Assignees: Universite de Bordeaux, Bordeaux (FR); INSERM (Institut National de la Santé et de la Recherche Medicale), Paris (FR); Fondation Bordeaux Universite, Bordeaux (FR)

( * ) Notice: Subject to any disclaimer, the term of this patent is extended or adjusted under 35 U.S.C. 154(b) by 182 days.

(21) Appl. No.: 18/553,454

(22) PCT Filed: Mar. 31, 2022

(86) PCT No.: PCT/FR2022/050611
§ 371 (c)(1),
(2) Date: Sep. 29, 2023

(87) PCT Pub. No.: WO2022/208030
PCT Pub. Date: Oct. 6, 2022

(65) Prior Publication Data

US 2024/0189038 A1 Jun. 13, 2024

(30) Foreign Application Priority Data

Mar. 31, 2021 (FR) ...................................... 2103299

(51) Int. Cl.
*A61B 34/10* (2016.01)
*A61B 18/02* (2006.01)
(Continued)

(52) U.S. Cl.
CPC .............. *A61B 34/10* (2016.02); *A61B 18/02* (2013.01); *A61B 18/12* (2013.01); *A61B 18/18* (2013.01);
(Continued)

(58) Field of Classification Search
CPC ......... A61B 34/10; A61B 34/25; A61B 18/02; A61B 18/12; A61B 18/18; A61B 2034/107; A61B 2034/252
(Continued)

(56) References Cited

U.S. PATENT DOCUMENTS

2007/0239062 A1* 10/2007 Chopra ................ A61B 5/4381 600/549
2015/0038883 A1* 2/2015 Kurtz ................ G01R 33/4814 601/3
(Continued)

FOREIGN PATENT DOCUMENTS

CA 3075454 A1 4/2019
CN 109259822 A 1/2019
(Continued)

OTHER PUBLICATIONS

International Search Report for Application No. PCT/FR2022/050611 dated Jul. 5, 2022, 4 pages.
(Continued)

*Primary Examiner* — Ahmed M Farah
(74) *Attorney, Agent, or Firm* — TraskBritt

(57) ABSTRACT

An assembly for heat-treatment of biological tissue comprises: a thermal energy generator; an energy applicator; an MRI image acquisition device for generating anatomical images and phase images; a planning unit comprising an MRI image processing means for defining a target region, a region to be preserved, and a neutral region in the tissue, and for assigning a heat treatment setpoint and an acceptable
(Continued)

temperature measurement uncertainty to the three regions; a unit for monitoring evolution of the status of the heat treatment and for receiving data from the planning unit and from the MRI image acquisition device during a heat treatment, the monitoring unit comprising a means for generating temperature images from the phase images, a means for calculating a reliability indicator from the temperature variation indicated on the temperature image, and a means for calculating an indicator of the status of the heat treatment in the three regions.

22 Claims, 4 Drawing Sheets

(51) Int. Cl.

| | |
|---|---|
| ***A61B 18/12*** | (2006.01) |
| ***A61B 18/18*** | (2006.01) |
| ***A61B 34/00*** | (2016.01) |

(52) U.S. Cl.
CPC ........ *A61B 34/25* (2016.02); *A61B 2034/107* (2016.02); *A61B 2034/252* (2016.02)

(58) Field of Classification Search
USPC .............................................................. 606/1
See application file for complete search history.

(56) References Cited

U.S. PATENT DOCUMENTS

2017/0020605 A1* 1/2017 Ellsworth .............. A61N 1/403
2019/0247120 A1 8/2019 Greenwood et al.
2020/0166593 A1* 5/2020 Rinott .................... A61B 5/015
2020/0237424 A1* 7/2020 Hunziker ............... A61B 18/12
2021/0093897 A1 4/2021 Zadicario et al.

FOREIGN PATENT DOCUMENTS

CN 111200972 A 5/2020
CN 111511439 A 8/2020
WO 2019/077385 A1 4/2019
WO WO-2019069135 A1 * 4/2019 ....... G01R 33/56509
WO 2019/086921 A1 5/2019

OTHER PUBLICATIONS

International Written Opinion for Application No. PCT/FR2022/050611 dated Jul. 5, 2022, 9 pages.
CN Office Action, Including Search report received for Chinese Patent Application No. 202280026377.7, mailed on Apr. 15, 2026, 20 pages (11 pages of English Translation and 9 pages of Original Document).

* cited by examiner

HEAT TREATMENT ASSEMBLY

CROSS REFERENCE TO RELATED APPLICATIONS

This application is a national phase entry under 35 U.S.C. § 371 of International Patent Application PCT/FR2022/050611, filed Mar. 31, 2022, designating the United States of America and published as International Patent Publication WO 2022/208030 A1 on Oct. 6, 2022, which claims the benefit under Article 8 of the Patent Cooperation Treaty to French Patent Application Serial No. FR2103299, filed Mar. 31, 2021.

TECHNICAL FIELD

The present disclosure relates to the field of treating a biological tissue by localized variation in temperature under guidance by intraoperative imaging.

More specifically, the present disclosure relates to an assembly and a method allowing the quantification in real-time and in 3D of the temporal evolution of the heat treatment of the targeted biological tissue.

The heat treatment assembly and the associated method can be used during the intraoperative phase, in order to be able to display in real-time quantitative information indicating the volume in which a variation in the temperature has been induced in a target region and/or in neighboring regions of the target region.

BACKGROUND

It is known to treat pathological biological tissues locally by targeted administration of an increase in temperature (hyperthermia) or a decrease in temperature (hypothermia) by means of an energy source. For example, the energy may be provided by a laser, microwaves, radio-frequency waves, focused ultrasound or by cryotherapy.

Among these techniques, a first category of heat treatment is distinguished, which consists in depositing an energy dose in a target area of a biological tissue via energy generator means positioned remotely (focused ultrasounds or radio-frequency waves by induction) or in the target area by percutaneous or vascular route (radio-frequency, laser, microwave, cryotherapy). Most devices propose a pre-defined implementation aimed at reaching a given volume a priori. However, the volume actually treated might substantially vary because of physiological/physiopathological parameters (perfusion, thermal diffusivity, energy absorption, presence of large vessels nearby, tissue and cell heterogeneity).

Prior to the heat treatment, a phase referred to as "pre-operative planning phase" is intended to assess the 3D extension of the affected area thanks to suitable imaging techniques, for example, by computed tomography (which may be designated by "TDM" throughout the present description) or by Magnetic Resonance Imaging (which may be designated by "MRI" throughout the present description), able to determine the size, the number, the location and the shape of the target region(s).

During this pre-operative planning phase, global indicators of the dimensions of the area to be treated, their number and their relative location with respect to identifiable anatomical references are generally defined.

At the beginning of the treatment, a ballistic phase involves positioning the energy generator device opposite the region to be treated. In general, this positioning is performed iteratively using an intermittent imaging guidance.

During the treatment phase, the energy deposition is generally performed with a monitoring (echography, physiological signals, sensors integrated into the treatment device), which does not enable an accurate quantification of the 3D distribution of the temperature in the region to be treated. In some particular cases, in particular focused ultrasound treatments guided by MRI, the temperature variation in the region to be treated is globally displayed and the energy deposition could be interrupted when it deviates from the setpoint. From the imaging of the temperature, it is possible to calculate a thermal dosimetry, which is a reliable indicator of the treatment, provided that the uncertainty on the thermometry is less than or equal to 1° C. in each pixel of the image.

In the absence of any temperature imaging modality, point measurements of the temperature may be provided by invasive sensors (probes implanted in the tissue and/or in the therapeutic device).

Although the heat treatment technique is much less invasive than surgery, it has some limitations. One of the general problems of the localized heat treatment is the lack of real-time, 3D and accurate monitoring of the temperature in the biological tissues.

The deviation between the planned and actual energy deposition in the different regions might be accentuated by the ballistic errors such as, for example, an imperfect positioning of the energy applicator opposite the region to be treated.

Consequently, the actual energy deposition might substantially deviate from the planned energy deposition.

One consequence of this effect is an incomplete treatment associated with risks of recurrence of the pathology.

Likewise, the risks of altering healthy tissues of the region to be preserved are accentuated, which could give rise to serious side effects.

Consequently, the number of patients eligible for these minimally or non-invasive therapies is considerably reduced due to the lack of accurate intraoperative monitoring of the therapy.

The lack of 3D monitoring of the treatment accurately and in real-time makes it difficult to adjust these thermotherapies, in particular the accurate repositioning of the energy applicator to complete the treatment by one or more additional successive energy deposition(s) in the region(s) not yet treated. Consequently, the practitioner assesses the effectiveness of the treatment a posteriori, i.e., immediately after the procedure or up to several weeks after the procedure, which does not allow for an optimal treatment in one single procedure, resulting in a loss of efficiency and a risk of loss of chance for the patient.

Current methods do not propose accurate and real-time monitoring of the surrounding regions of the region to be treated, which increases the risks of per- and post-operative complications.

BRIEF SUMMARY

Hence, the present disclosure aims to propose an assembly and a method that allow, during the intraoperative treatment phase, real-time monitoring, with a refresh rate of one second or better, in 3D, encompassing the entire biological tissue to be treated and its surrounding and quantitative of the temperature.

The heat treatment assembly of the present disclosure enables a quantitative and dynamic monitoring of the treatment of the targeted biological tissue by proposing quantitative indicators related to the treatment. It aims to improve the efficiency of the heat treatment as well as its safety and therefore to increase the benefit/risk balance of these thermotherapies. Another expected consequence of the present disclosure is to increase the number of patients eligible for these therapies having less side effects than conventional surgery and better efficiency than drug treatments.

In accordance with embodiments of the present disclosure, a heat treatment assembly is provided for a target region of a biological tissue comprising:

a thermal energy generator;

an energy applicator coupled to the generator and configured to deposit thermal energy in the target region so as to induce a temperature variation;

an MRI image acquisition device configured to generate at least one MRI anatomical image (IMG_IRM_A) and at least one phase image (IMG_IRM_P);

a planning unit comprising an MRI image processing means configured to define the target region Rc, a region to be preserved Rp and a neutral region Rn on the at least one MRI anatomical image (IMG_IRM_A), the MRI image processing means being also configured to assign a heat treatment setpoint to each of the three regions and an acceptable temperature measurement uncertainty to each of the three regions;

a unit for monitoring the evolution of the status of the heat treatment configured to receive data originating from the planning unit and data originating from the MRI image acquisition device in real-time during a heat treatment phase, the monitoring unit comprising a means for generating temperature images from the at least one phase image (IMG_IRM_P), a means for calculating a reliability indicator of the temperature variation indicated on the temperature image and a means for calculating an indicator of the status of the heat treatment in each of the three regions;

the means for calculating a quantitative indicator of the status of the heat treatment (12) being configured to:

spatially match the MRI anatomical image with the temperature images generated during the heat treatment;

compare the temperature and/or the thermal dose associated with each pixel of the three regions with the predefined heat treatment setpoint in each of the three regions;

determine the number of pixels that meet the predefined heat treatment setpoint for each of the three regions, the number corresponding to the quantitative indicator of the status of the heat treatment in real-time;

generate in real-time signals indicative of the status of the heat treatment and the temporal evolution of the quantitative indicators in the three regions.

Thus, the practitioner can follow during the thermal treatment in real-time and continuously the evolution of the quantitative indicators in the three regions. The signal is presented, for example, in the form of a 2D or 3D map, or a graphical representation. The dynamic display of the number of pixels having reached the predefined temperature setpoint and/or the thermal dose setpoint enables the practitioner to monitor the evolution of the treatment not only in the target region but also in the region to be preserved and the neutral region and assists the practitioner in making a decision in real-time during the treatment.

In the target region, the number of pixels that meet the predefined heat treatment setpoint may be compared with the number of predefined pixels in the target region before the beginning of the treatment to provide a percentage of treated volume.

In the neutral region, the number of pixels that meet the predefined heat treatment setpoint may be compared with the number of predefined pixels in this region in order to provide a percentage of alteration volume, which should ideally remain as close to zero as possible.

In the critical region to be preserved, no pixel should violate the predefined set point(s). Hence, it is necessary to provide an early indicator of the risk of violation of these instructions. Consequently, an alert signal, for example, an audible alert signal, may be given, for example, when 80% of the lethal thermal dose is reached in one or more pixel(s) of this region, or when the temperature approaches a few degrees from the authorized limit temperature.

In the neutral region, the alert signal may also be given with similar or different alert signals, but with a lesser criticality, since it is acceptable (even though not desirable) to violate the set point(s) in this region.

These alert signals allow warning the practitioner in real-time on the risk of creating alterations in the neutral and critical regions to be preserved before the setpoints are reached or exceeded in the neutral and critical regions to be preserved.

The signals indicative of the status of the heat treatment generated in real-time at each new temperature measurement and thermal dose may be visual or audible to indicate the treatment status in the three regions.

The features disclosed in the next paragraphs may optionally be implemented. They may be implemented independently of one another or in combination with one another:

The assembly further comprises a second image acquisition device configured to generate at least one anatomical image (IMG_A).

The planning unit further comprises an anatomical image processing means configured to define the three regions on the anatomical image (IMG_A), a recalibration means configured to spatially match the anatomical image with the MRI anatomical image originating from the MRI image acquisition device.

The means for calculating a reliability indicator is configured to:

determine the uncertainty of the measured temperature in each region from a temperature variance determined over a series of temperature images;

determine a number of pixels in each of the three regions that meet the predefined acceptable temperature measurement uncertainty, the number corresponding to the indicator of reliability of the temperature variation indicated on the temperature image.

According to one embodiment, the means for calculating a quantitative indicator of the status of the heat treatment is configured to exclude the pixels whose measured temperature variation is not usable or reliable. This allows increasing the reliability of the quantitative indicator generated by the calculation means, in particular while avoiding generating inadvertent alert signals during the treatment.

According to one embodiment, the heat treatment setpoint assigned to the target region Rc corresponds to a minimum temperature to be reached, a minimum thermal dose to be reached, or a predefined curve of the evolution of the temperature over the time.

According to another embodiment, the heat treatment setpoint assigned to the region to be preserved Rp corresponds to a maximum temperature not to be exceeded or a maximum thermal dose not to be exceeded.

According to still another embodiment, the heat treatment setpoint assigned to the neutral region corresponds to a maximum temperature not to be exceeded or a maximum thermal dose not to be exceeded.

According to one embodiment, the energy applicator is a laser beam applicator, a microwave applicator, a radio-frequency wave applicator, a focused ultrasonic applicator or a cryogenic energy applicator.

Advantageously, the assembly further comprises a display unit configured to display the quantitative indicators of the status of the treatment in each of the three regions.

According to another aspect, a method is provided for real-time quantitative monitoring of the status of the heat treatment of a biological tissue implementing the heat treatment assembly as defined hereinabove, the method comprising the following steps:

- generating at least one MRI anatomical image;
- defining a target region Rc, a region to be preserved Rp and a neutral region Rn on the MRI anatomical image;
- determining a first set of target pixels within the target region, a second set of pixels to be preserved within the region to be preserved Rp, and a third set of neutral pixels within the neutral region Rn;
- assigning a heat treatment setpoint to each of the pixels in the three regions Rc, Rp and Rn;
- assigning an acceptable temperature measurement uncertainty to each of the pixels in the three regions Rc, Rp and Rn;
- determining the reliability indicator of the temperature variation indicated on a temperature image, the reliability indicator corresponding to the number of pixels meeting the predefined uncertainty in the three regions;
- generating temperature images from the phase images transmitted by the MRI image acquisition device;
- calculating the quantitative indicator of the status of the heat treatment, the indicator corresponding to the number of pixels or the percentage of pixels that meet the predefined heat treatment setpoint for each of the three regions Rc, Rp and Rn;
- displaying in real-time the 3D temperature map and the 3D thermal dose map, the quantitative indicator of the status of the heat treatment in each of the three regions.

According to one embodiment, the method further comprises a planning phase carried out before the thermal pretreatment phase, the planning phase comprising the following steps:

- generating at least one anatomical image (IMG_A);
- defining the target region Rc, the region to be preserved Rp and the neutral region Rn on the anatomical image;
- determining a first set of target pixels within the target region, a second set of pixels to be preserved within the region to be preserved Rp, and a third set of neutral pixels within the neutral region Rn;
- and the pretreatment phase further comprises a step of recalibration between the anatomical image and the MRI anatomical image in order to define the three regions on the MRI anatomical image.

Advantageously, the display step generates a visual and/or audible indicator indicating that the heat treatment is completed in the region Rc when the number of pixels of the region Rc meeting the treatment setpoint reaches a predefined threshold.

Advantageously, the display step generates a visual and/or audible indicator indicating that the safety setpoint in the region Rp is not complied with when the number of pixels of the region to be preserved not meeting the predefined setpoint is greater than a predefined threshold.

BRIEF DESCRIPTION OF THE DRAWINGS

Other features, details and advantages of the present disclosure will appear upon reading the detailed description hereinafter of example embodiments of the present disclosure, and upon analyzing the appended drawings, wherein.

DETAILED DESCRIPTION

Figure 1:
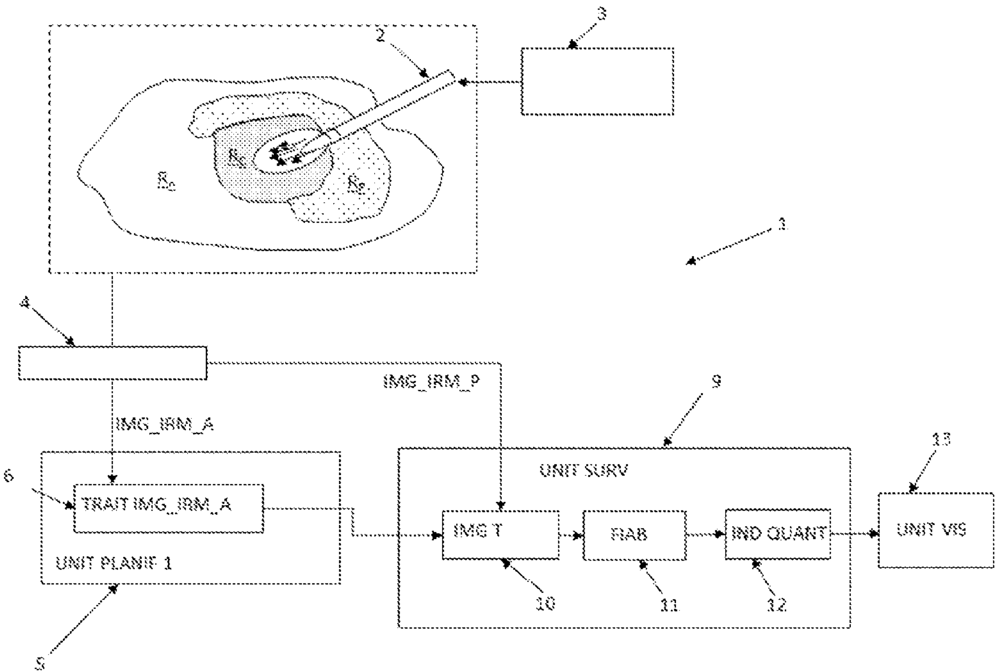
FIG. 1 schematically represents a heat treatment assembly according to one embodiment.

In the context of the present disclosure, by "target region," it should be understood a region comprising the pathological tissue to be treated visible in imaging and a region that surrounds the pathological tissue. The extent of the neighborhood around the pathological tissue is variable and is defined by the practitioner. The target region should undergo a temperature variation in order to treat the pathological tissue. The region is designated by Rc in FIG. 1.

In the context of the present disclosure, by "critical region to be preserved," it should be understood a region in which the biological tissue is healthy and which should not undergo a deleterious temperature variation during the heat treatment. The region is designated by Rp in FIG. 1.

In the context of the present disclosure, by "neutral region," it should be understood a region in which the biological tissue is healthy and should ideally not undergo a temperature variation during the heat treatment. Nonetheless, a possible temperature variation is not considered to be critical for the patient. The region is designated by Rn in FIG. 1.

In the context of the present disclosure, a 3D anatomical image is a reconstructed image representing the anatomy of the target region and its environment. This 3D anatomical image may be obtained by different imaging techniques.

In the context of the present disclosure, the Magnetic Resonance Imaging (MRI) device is a device configured to provide information regarding the target, critical and neutral regions. This information may be anatomical and/or functional in nature. The information may in particular relate to the variations in the temperature of the tissues contained in the aforementioned regions. To do so, the magnetic resonance imaging device generates 3D MRI images and associates with each voxel of the MRI image (elementary volume unit of each region) a complex number $M.e^{\Phi}$, where M is the modulus and $\Phi$ the phase of the magnetization vector in this voxel. In the remainder of the description and in the context of the present disclosure, the term "pixel" of an image represents one or more information of the associated voxel. The module M in each pixel of the image enables the construction of an MRI anatomical image IMG_IRM_A. The phase difference between two consecutive MRI phase images IMG_IRM_P is directly proportional to a temperature difference, thereby allowing the construction of a temperature image.

In the context of the present disclosure, the "thermal dose" corresponds to the integration of the temperature over time. Thus, a thermal dose map can be obtained from a temperature map. The temperature and thermal dose maps obtained during the treatment are indicators of the biological effect induced by the thermal dose.

For the most part, the drawings and the description hereinafter contain certain elements. Hence, they could not only be used to better understand this disclosure, but also contribute to the definition thereof, where applicable.

FIG. 1 represents an assembly 1 for heat treatment of a target region Rc to be treated of a biological tissue according to an embodiment of the present disclosure. The assembly 1 comprises a heat treatment device comprising an applicator 2 coupled to a thermal energy generator 3, an MRI image acquisition device 4, a planning unit 5 (UNIT PLANIF 1), a unit 9 (UNIT SURV) for monitoring in real-time the status of the heat treatment by generating at least one quantitative indicator of the status of the heat treatment and a display unit 13 (UNIT VIS).

The thermal energy applicator 2 is configured to induce a variation in temperature in the target region Rc to be treated of the biological tissue. The thermal energy applicator 2 may consist of a radio-frequency wave applicator, a microwave applicator, a focused ultrasound applicator, an applicator of a laser beam or a cryogenic energy applicator. In FIG. 1, a percutaneous applicator is schematically shown positioned within the target region Rc to be treated. The thermal energy applicator 2 is powered by the energy generator 3. The thermal energy applicator may also be in the form of a non-invasive extracorporeal transmitter (focused ultrasounds, inductive radio-frequencies), which is adapted to focus a deposition of thermal energy in the target region.

The MRI image acquisition device 4 is used during a pretreatment phase to generate MRI anatomical images (IMG_IRM_A). The pretreatment phase is a phase carried out just before the beginning of the heat treatment. Afterwards, the MRI anatomical images (IMG_IRM_A) are transmitted to the planning unit 5.

The MRI image acquisition device 4 is also used to generate phase images (IMG_IRM_P) from a sequence of images sensitive to the temperature variation acquired throughout the duration of the heat treatment. The MRI imaging device 4 is configured to obtain dynamic temperature imaging encompassing the three predefined regions Rc, Rp and Rn, throughout the duration of the heat treatment. This dynamic imaging is obtained using a fast acquisition sequence, in the range of the second or less for each acquired volume, with a spatial resolution in the range of one millimeter or better. The phase images (IMG_IRM_P) are transmitted to the monitoring unit 9.

The planning unit 5 comprises a means for processing MRI anatomical images 6 (TRAIT IMG_IRM_A), which is configured to define on the 3D MRI anatomical image the target region Rc, the critical region to be preserved Rp and the neutral region Rn.

For example, a biological tissue is schematically represented in FIG. 1 comprising a target region, called Rc, surrounded by a critical region to be preserved, called Rp and a neutral region, called Rn. The target region Rc should contain the entirety of the pathological area to be treated and not include the critical region to be preserved.

According to one embodiment, the means for processing MRI anatomical images 6 is able to segment the 3D MRI anatomical image in order to determine in the region Rc the target pixels, in the critical region to be preserved, the pixels to be preserved, in the neutral region, the neutral pixels.

The means for processing MRI anatomical images 6 is also configured to define a heat treatment instruction in each of the three regions. More specifically, the means for processing MRI anatomical images 6 is configured to assign to each of the pixels of each of the three regions a temperature and/or thermal dose setpoint to be observed.

In the target region Rc, the heat treatment setpoint may be either a minimum temperature to be reached, or a minimum thermal dose to be reached, or a predefined curve of the evolution of the temperature over time, or a combination of several temperature and thermal dose setpoints.

In the critical region to be preserved Rp, the heat treatment setpoint may be either a maximum temperature not to be exceeded, or a maximum thermal dose not to be exceeded.

In the neutral region Rn, the heat treatment setpoint may be either a maximum temperature not to be exceeded, or a maximum thermal dose not to be exceeded.

According to an embodiment of the present disclosure, the means for processing MRI anatomical images 6 is also configured to define an uncertainty of the acceptable temperature measurements in each of three regions. More specifically, it is configured to assign to each of the pixels determined in each of the three regions Rc, Rp and Rn an acceptable uncertainty for the temperature measurement. The value of the uncertainty may be related to the predefined temperature setpoint. For example, when a temperature variation of 5° C. is defined in the region Rc, it is not acceptable, for example, to have an uncertainty greater than 3° C.

The MRI anatomical images (IMG_IRM_A) with the information associated with each of the three regions are transmitted to the monitoring unit 9.

The associated information is the temperature and/or thermal dose setpoints and the uncertainties of the acceptable temperature measurements assigned to each of the pixels determined in the three region Rc, Rp and Rn.

The monitoring unit 9 is configured to receive in real-time during the heat treatment of the phase images (IMG_IRM_P) originating from the MRI image acquisition device 4 and to generate a quantitative indicator of the evolution of the heat treatment in real-time during the heat treatment from the MRI anatomical images (IMG_IRM_A) and from the phase images (IMG_IRM_P).

Advantageously, the monitoring unit 9 is also configured to receive measurements originating from internal sensors integrated into the heat treatment device (not illustrated in FIG. 1) and additional external sensors (not illustrated in FIG. 1). For example, the internal sensors may be sensors integrated into the thermal energy applicator 2 to transmit information on its position in space with respect to the target region, the thermal energy sent by the applicator and/or point measurements of the temperature obtained by temperature sensors. For example, the measurements originating from additional external sensors may comprise physiological measurements, for example, measurements relating to breathing, cardiac activity and to the position of the patient.

The monitoring unit 9 is configured to process the data it receives in real-time. The monitoring unit is configured so that the data analysis and processing rate is greater than that of the acquisition of the phase images by the MRI image acquisition device 4 to dynamically generate and with minimum latency the quantitative indicator representative of the evolution of the status of the heat treatment during the treatment phase.

The monitoring unit 9 comprises a means 10 for generating temperature images (IMG T) from the phase images (IMG_IRM_P) acquired by the MRI image acquisition device 4. The temperature image generation means 10 further comprises an algorithm adapted to compensate for the movement artifacts, time and spatial drift of the MRI imaging device and also integrates the analysis of the data originating from the external sensors of the heat treatment device and the data originating from the additional sensors, for example, the physiological sensors.

The monitoring unit 9 comprises a means for calculating the reliability indicator of the thermometry 11 (FIAB). Thermometry designates the temperature variation indicated on the temperature image generated from the MRI phase images. The calculation of the reliability indicator of the thermometry is implemented before the deposition of energy by the energy applicator. The calculation means 11 is configured to determine the uncertainty of the temperature in each pixel from a variance of the temperature measured, for example, over a series of several successive temperature images. For example, the series may comprise ten successive temperature images to calculate the variance. According to one embodiment, the reliability indicator calculation means can generate a 2D or 3D map representing the pixels that meet the predefined acceptable uncertainties in the planning unit 5. The calculation means 11 is able to determine the reliability indicator, i.e., the number or the percentage of pixels that meet the predefined uncertainties in the planning unit 5.

The reliability indicator calculation means 11 is configured to compare the determined reliability indicator with a threshold predefined by the practitioner.

According to a first configuration, when the reliability indicator is less than a predefined threshold, the reliability indicator calculation means 11 is able to generate a control signal to indicate that the temperature variation indicated on the temperature image is not reliable to calculate the quantitative indicator of the status of the heat treatment and to start monitoring of the heat treatment. The control signal is a visual signal transmitted to the display unit 13 and/or an audible signal. The monitoring process is stopped and it is not possible for the practitioner to start the heat treatment.

According to a second configuration, when the reliability indicator is less than the predefined threshold, the reliability indicator calculation means 11 generates a signal indicating that the temperature variation indicated on the temperature image is not reliable to calculate the quantitative indicator of the status of the heat treatment and to start monitoring of the heat treatment. Nonetheless, the decision to start the heat treatment or not is taken by the practitioner.

According to still another configuration, when the reliability indicator is less than the predefined threshold but remains within a range of acceptable values for the practitioner to continue the heat treatment, the reliability indicator calculation means 11 is able to generate a signal inviting the practitioner to modify the MRI image acquisition parameters and/or to apply a filtering to reduce the value of the variance of the measured temperature. In this way, the practitioner can manually adjust the different parameters to find acceptable thermometry conditions to start monitoring and carry out the heat treatment.

The monitoring unit 9 comprises a means for calculating a quantitative indicator of the status of the heat treatment 12 (IND QUANT) from the temperature images and the MRI anatomical images with the associated information originating from the planning unit 5.

In a first calculation step, the means for calculating the quantitative indicator 12 determines the temperature and the thermal dose in each of the pixels of the regions Rc, Rp and Rn. To do so, the calculation means spatially match the MRI anatomical image generated before the heat treatment originating from the planning unit 5 and the temperature images generated during the heat treatment. In this way, the pixels defined in the three regions Rc, Rp and Rn on the MRI anatomical image are associated with the pixels of the generated temperature images.

According to the present disclosure, by "spatial matching" of images, it should be understood any operation that consists in matching at least two images in order to be able to compare or combine their respective information.

In a second calculation step, the quantitative indicator calculation means 12 determines in real-time during the heat treatment the number or the percentage of pixels meeting the predefined treatment setpoints in the planning unit for the three regions Rc, Rp and Rn. The means for calculating quantitative indicators 12 compares pixel-by-pixel on the temperature image the value of the temperature variation with the temperature setpoint assigned to the pixel of the corresponding region.

In the determination of the number of pixels that meet the heat treatment setpoints, the calculation means 12 is able to exclude the pixels considered to have no usable or reliable temperature measurement. For example, the excluded pixels have an uncertainty greater than the predefined uncertainty in the planning unit. According to another example, the excluded pixels have a signal-to-noise ratio of the modulus close to zero and therefore with an undefined phase. Hence, it is not possible to give reliable information on compliance with the setpoint in these pixels. This information is transmitted to the practitioner so that they may make an informed decision on the conduct of the treatment.

Advantageously, the calculation means 12 is configured so as to obtain a speed of processing the data originating from the MRI imaging device 4 and of the data originating from the planning unit 5 faster than the speed of acquisition of the modulus and phase images in order to be able to process the temperature images dynamically and without latency.

The monitoring unit 9 transmits in real-time to the display unit 13 all the data at the output of the monitoring unit, such as the temperature and thermal dose maps, the quantitative indicator of the status of the heat treatment, as well as the data of the physiological sensors and those of the sensors integrated into the heat treatment device, for a real-time display to the practitioner so that he could monitor the evolution of the heat treatment, to decide on the continuation or possible stoppage of the heat treatment according to the status of the heat treatment corresponding to the predefined treatment setpoints.

According to one embodiment, the display of the quantitative indicators of the heat treatment may take various forms. For example, the pixels having reached the temperature setpoint defined in the target region Rc are represented with a predefined colorimetric coding, enabling a 2D or 3D visualization with a high accuracy of reading of the volume treated during the treatment. This information is complementary to the display of the temperature maps and of thermal doses superimposed on the MRI anatomical images.

The display unit 13 further comprises means for generating visual and/or audible indicators indicating:

- that the treatment is terminated in the Rc region when the number of pixels of the region Rc meeting the defined temperature setpoint in the region Rc reaches a predefined threshold;
- that the temperature setpoint in the region Rp is not observed;
- that the temperature setpoint in the region Rn is not respected.

Figure 2:
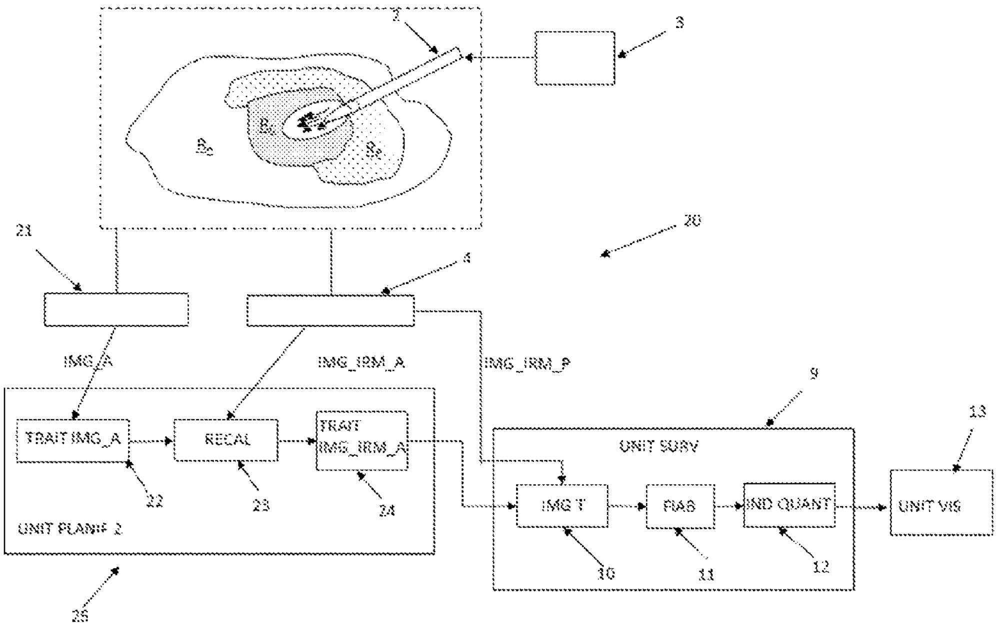
FIG. 2 schematically represents a heat treatment assembly according to another embodiment.

FIG. 2 illustrates a heat treatment assembly 20 according to another embodiment.

The heat treatment assembly 20 comprises a heat treatment device comprising an applicator 2 coupled to a thermal energy generator 3, a device 4 for acquiring MRI images for generating magnetic resonance images, an imaging device 21 for generating anatomical images (IMG_A), a planning unit 25 (UNIT PLANIF 2), a unit 9 for monitoring (UNIT SURV) in real-time the status of the heat treatment by generating a quantitative indicator of the status of the heat treatment and a display unit 13 (UNIT VIS).

Like in the first embodiment, the thermal energy applicator 2 is configured to induce a variation in temperature in the target region Rc to be treated of the biological tissue. The MRI image acquisition device 4 is used during a pretreatment phase to generate MRI anatomical images (IMG_IRM_A) and phase images (IMG_IRM_P) during the heat treatment. The MRI anatomical images (IMG_IRM_A) are transmitted to the planning unit 25 and the MRI phase images (IMG_IRM_P) are transmitted to the monitoring unit 9.

For example, the imaging device 21 may be another MRI image acquisition device, a Computerized Tomography (TDM) or an ultrasound echography (US). Thus, the anatomical image (IMG_A) may be generated, for example, during a planning phase, before the day of the heat treatment. Anatomical images may also be generated from a pre-computed 3D model from imaging data or other data, such as, for example, a 3D mapping of the cardiac electrical signal. The anatomical images (IMG_A) are transmitted by the imaging device 21 to the planning unit 25.

The planning unit 25 comprises a means for processing anatomical images 22 (TRAIT IMG_A), a recalibration means 23 (RECAL) and a means for processing MRI images 24 (TRAIT IMGJRM).

The means for processing anatomical images 22 is configured to define the three regions Rc, Rp and Rn on the anatomical image IMG_A generated by the imaging device 21 during the planning phase. More specifically, the anatomical image processing means 22 is adapted to segment the anatomical image IMG_A in order to determine in the region Rc the target pixels, in the region to be preserved, the pixels to be preserved and in the neutral region, the neutral pixels. The anatomical image IMG_A with the three delimited regions is transmitted to the recalibration means 23.

The recalibration means 23 is configured to spatially match the anatomical image (IMG_A) with the MRI anatomical image (IMG_IRM_A) generated just before the beginning of the treatment by the MRI imaging device 4, so as to define the three regions Rc, Rp and Rn on the MRI anatomical image (IMG_IRM_A). Afterwards, the MRI anatomical image with the three defined regions are transmitted to the MRI image processing means 24.

Like in the first embodiment, the MRI image processing means 24 is configured to define a heat treatment setpoint and an uncertainty of the acceptable temperature measurements in each of the three regions defined on the MRI anatomical images.

Afterwards, the MRI anatomical images (IMG_IRM_A) with the information associated with each of the three regions are transmitted to the monitoring unit 9. The information are the temperature and/or thermal dose setpoints and the uncertainties of the acceptable temperature measurements assigned to each of the pixels determined in the three region Rc, Rp and Rn.

The operation of the monitoring unit 9 is identical to the first embodiment illustrated in FIG. 1 and described hereinbelow and will not be detailed herein.

Likewise, the operation of the display unit 13 is identical to the first embodiment illustrated in FIG. 1 and described hereinbelow.

The present disclosure also relates to a method for real-time monitoring of the status of the heat treatment, by generating in real-time a quantitative indicator of the status of the heat treatment, on the volume treated with respect to the total volume of the target region to be treated and for assisting the practitioner in his decision-making. The indicator enables the practitioner to view the progress over time of the deposition of thermal energy and of the volume treated. The method is implemented in accordance with the steps described hereinbelow using a heat treatment assembly in accordance with the present disclosure.

Figure 3:
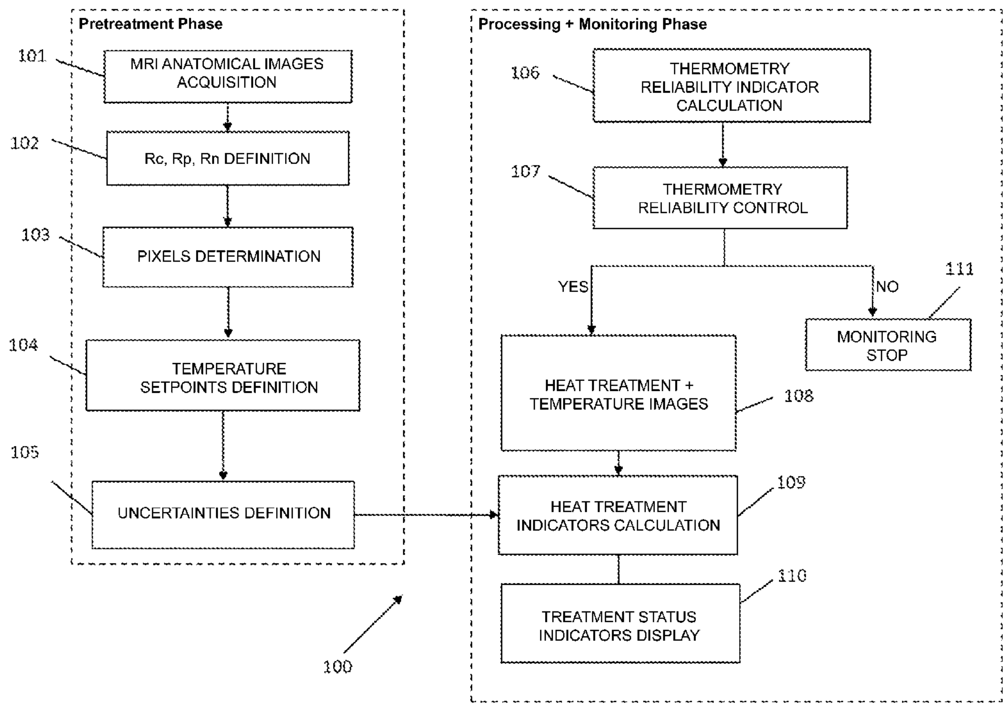
FIG. 3 is a flowchart representing the method for monitoring the heat treatment according to one embodiment.

Referring to FIG. 3, a method implementing a heat treatment assembly of FIG. 1 is described hereinabove.

The method comprises a pretreatment phase and a heat treatment phase.

During the pretreatment phase, the planning unit 5 generates MRI anatomical images (IMG_IRM_A) with the defined three regions Rc, Rp and Rn and information associated with each of the pixels determined in the three regions. The information comprise predefined treatment instructions for each of the three regions and predefined temperature measurement uncertainties in each of the three regions. This pretreatment phase is carried out just before the heat treatment phase.

During the treatment phase, the monitoring unit 9 calculates quantitative indicators on the status of the heat treatment from the data originating from the pretreatment phase and the temperature images generated during the heat treatment.

The pretreatment phase comprises a step 101 of acquiring a 3D MRI anatomical image of the target region and its environment. The 3D MRI anatomical images are obtained with the MRI imaging device 4.

The pretreatment phase comprises a step 102 of defining a target region Rc, a critical region to be preserved Rp and a neutral region on the MRI anatomical image.

The method comprises a step 103 of determining the pixels in each of the defined regions. This step consists in segmenting the MRI anatomical image so as to determine a first set of target pixels inside the target region, a second set of pixels to be preserved inside the region to be preserved, and a third set of neutral pixels inside the neutral region.

The method comprises a step 104 of assigning to each of the pixels a temperature and thermal dose setpoint to be observed for each of the three defined regions.

The method comprises a step 105 of assigning to each of the pixels an acceptable uncertainty for the temperature measurement for each of the three regions defined on the MRI anatomical images (IMG_IRM_A).

The MRI anatomical images, the defined temperature setpoints and the temperature measurement uncertainties defined in the three regions Rc, Rp and Rn are transmitted to the monitoring unit 9.

The method comprises a step 106 of calculating the reliability indicator of the thermometry before starting the heat treatment, i.e., just before the deposition of energy by the applicator 2. The thermometry reliability indicator calculation step comprises the following sub-steps:

- generating a series of temperature images from the phase images transmitted by the MRI imaging device 4, the phase images being acquired without deposition of thermal energy in the target region;

spatially matching the temperature images with the MRI anatomical image transmitted by the planning unit 5 to define the three regions Rc, Rp, Rn on the temperature images;

determining a variance of the temperature measured for each of the pixels in the three regions;

calculating the uncertainty of the temperature measurement from the variance in each pixel;

comparing the predefined uncertainty in the planning unit 5 and the determined uncertainty for each pixel of the three regions;

determining the number of pixels meeting the predefined uncertainties, this number being representative of the reliability indicator of the temperature variation indicated on the temperature image.

According to one embodiment, it is possible to generate a map representing the three regions showing the pixels that meet the uncertainties predefined by the planning unit and the pixels that do not meet the uncertainties predefined by the planning unit.

The method comprises a step 107 of controlling the reliability indicator of the thermometry. In particular, the monitoring unit controls whether the reliability indicator of the thermometry is acceptable, i.e., whether the number of pixels meeting the predefined uncertainties is enough to start the heat treatment with a quantitative monitoring of the evolution of the heat treatment implemented by the monitoring unit 9.

According to one embodiment, when the reliability indicator calculated in step 106 is less than a predefined threshold, the reliability indicator calculation means 11 is able to generate a control signal to indicate that the temperature variation indicated on the temperature image is not reliable to calculate the quantitative indicator of the status of the heat treatment and to start monitoring. It is not possible for the practitioner to start the heat treatment. This is the step 111 of stopping the treatment process.

According to still another embodiment, when the reliability indicator is less than a predefined threshold but remains within a range of acceptable values for the practitioner to continue the heat treatment, the reliability indicator calculation means 11 is able to generate a signal inviting the practitioner to modify the MRI image acquisition parameters and/or to apply a filtering to reduce the value of the variance of the temperature. In this way, the practitioner can manually adjust the different parameters to find acceptable thermometry conditions for carrying out the heat treatment.

When the determined reliability indicator is greater than a predefined threshold by the practitioner, the practitioner can start the heat treatment. The monitoring unit 9 is also activated to monitor the evolution of the status of the heat treatment in real-time during the heat treatment. The monitoring unit 9 is synchronized with the heat treatment device, which deposits the thermal energy in the target region so as to start the heat treatment in the target region at the same time as the monitoring of the status of the heat treatment.

Hence, the monitoring phase comprises a step 108 in which the generation of the temperature images and the heat treatment are synchronized. The temperature images are generated from the phase images transmitted by the MRI imaging device 4 to the monitoring unit 9 in real-time during the heat treatment.

The monitoring phase comprises a step 109 of calculating the indicator of the status of the heat treatment in real-time. This indicator corresponds to the number of pixels meeting the predefined temperature setpoints for the three regions. To do so, the calculation means 12 spatially match the generated MRI anatomical image before the heat treatment originating from the planning unit and the temperature images generated during the heat treatment. In this manner, the pixels defined in the three regions Rc, Rp and Rn on the 3D MRI anatomical image are associated with the pixels of the generated temperature images. The temperature image generated during the heat treatment is compared pixel-by-pixel with the predefined temperature setpoints in order to determine the number of pixels meeting the predefined treatment setpoints for the three regions Rc, Rp and Rn.

According to an embodiment of the present disclosure, the pixels considered to have no usable or reliable temperature measurement are excluded when counting the number of pixels meeting the treatment setpoints.

The method comprises a step 110 of displaying the indicator of the status of the heat treatment in the three regions Rc, Rp and Rn. The indicators may be expressed in various ways, for example, as treated pixels or volume or as a percentage of treated volume with respect to the volume of the considered region. These indicators are displayed in real-time on a display interface to inform the practitioner on the evolution of the status of the heat treatment. For example, the pixels having reached the temperature setpoint in the target region are represented with a predefined colorimetric coding, enabling a 2D or 3D visualization with a high accuracy of reading of the volume treated during the treatment. The dynamic display of the number of pixels having reached the predefined temperature setpoint enables him to monitor the evolution of the treatment not only in the target region but also in the region to be preserved and the neutral region and assists him in making a decision according to the status of the heat treatment. The display interface also enables a display of 2D or 3D maps of temperatures and thermal doses superimposed on the anatomical images.

According to an embodiment of the present disclosure, the monitoring unit 9 generates a visual or audible indicator indicating that the heat treatment is completed when the number of pixels having reached the setpoint in the target region reaches a predefined threshold (for example, 100% of the number of pixels counted in the target region).

Likewise, the monitoring unit generates a visual and/or audible indicator signal when one or more of pixels not complying with the setpoint in the critical region to be preserved Rp, or when the temperature approaches a few degrees from the authorized limit temperature.

Likewise, the monitoring unit generates a visual and/or audible indicator signal when the number of pixels not complying with the setpoint in the neutral region reaches a predefined threshold, for example, when the percentage of alteration volume is close to 5%.

The method for quantitative monitoring of the evolution of the status of the heat treatment of the present disclosure is implemented during the heat treatment, allow providing a mapping of the treated volume in real-time.

Figure 4:
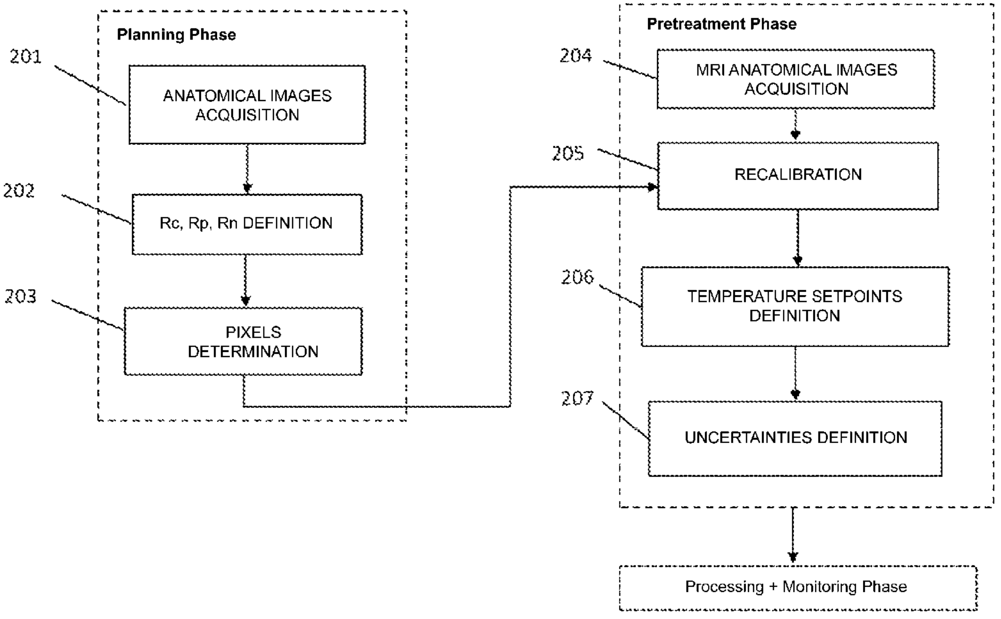
FIG. 4 is a flowchart representing the method for monitoring the heat treatment according to another embodiment.

Referring to FIG. 4, a method according to another embodiment implementing the heat treatment assembly of FIG. 2 is described hereinabove.

The method comprises a planning phase, a pretreatment phase and a heat treatment phase.

The planning phase is carried out before the day of the heat treatment and comprises a step 201 of acquiring 3D anatomical images (IMG_A), for example, by a TDM or US imaging device or generated from a pre-calculated 3D model from imaging data. During this planning phase, the practitioner also determines the characteristics of the target region in order to plan for the treatment; locate the target region, select the suitable thermal energy applicator.

The planning phase comprises a step 202 of defining a target region Rc, a critical region to be preserved Rp and a neutral region Rn on the 3D anatomical image by an anatomical image processing means 22.

The planning phase comprises a step 203 of determining target pixels in the target region Rc, pixels to be preserved in the region to be preserved Rp and neutral pixels in the neutral region Rn.

The pretreatment phase is carried out just before the heat treatment.

The pretreatment phase comprises a step 204 of acquiring MRI anatomical images by an MRI imaging device 4.

The pretreatment phase comprises a recalibration step 205 for spatially matching the anatomical image (IMG_A) acquired during the planning phase with the MRI anatomical image (IMG_IRM_A) so as to define the three regions Rc, Rp and Rn on the MRI anatomical image.

The pretreatment phase comprises a step 206 of defining heat treatment setpoints in each of the three regions defined on the MRI anatomical images (IMG_IRM_A). This step is similar to step 104 of the method according to a first embodiment described hereinabove.

The pretreatment phase comprises a step 207 of defining temperature measurement uncertainties in each of the three regions defined on the MRI anatomical images (IMG_IRM_A). This step is similar to step 105 of the method according to a first embodiment described hereinabove.

Afterwards, the 3D MRI anatomical images (IMG_IRM_A) with the information associated with each of the three regions are transmitted to the monitoring unit 9 for the heat treatment phase. The information are the temperature and/or thermal dose setpoints and the acceptable temperature measurements assigned to each of the pixels determined in the three regions Rc, Rp and Rn. The different steps forming the treatment phase are identical to those of the treatment phase of the method according to the first embodiment described hereinabove.

INDUSTRIAL APPLICATION

The heat treatment assembly according to the present disclosure with quantitative monitoring of the thermal energy deposition is particularly suitable for any type of treatments by local temperature variation. The present disclosure is particularly suitable for a treatment wherein the thermal energy is locally deposited by a laser, microwaves, radio-frequency waves, focused ultrasounds or cryotherapy.

The invention claimed is:

1. An assembly for heat treatment of a target region of a biological tissue comprising:

- a thermal energy generator;
- an energy applicator coupled to the generator and configured to deposit thermal energy in the target region so as to induce a temperature variation;
- a magnetic resonance imaging (MRI) image acquisition device configured to generate at least one MRI anatomical image and at least one MRI phase image;
- a planning unit comprising an MRI image processing means configured to define three regions including the target region, a region to be preserved, and a neutral region on the at least one MRI anatomical image, the MRI image processing means being configured to assign a heat treatment setpoint to each of the three regions and an acceptable temperature measurement uncertainty to each of the three regions;
- a unit for monitoring evolution of the status of the heat treatment and configured to receive data from the planning unit and data from the MRI image acquisition device in real-time during a heat treatment phase, the monitoring unit comprising a means for generating temperature images from the at least one MRI phase image, means for calculating a reliability indicator of the temperature variation indicated on the temperature image, and a means for calculating a quantitative indicator of the status of the heat treatment in each of the three regions;
- wherein the means for calculating a quantitative indicator of the status of the heat treatment is configured to:
  - spatially match the MRI anatomical image with the temperature images generated during the heat treatment;
  - compare the temperature and/or a thermal dose associated with each pixel of the three regions with the predefined heat treatment setpoint in each of the three regions;
  - determine the number of pixels that meet the predefined heat treatment setpoint for each of the three regions, the number corresponding to the quantitative indicator of the status of the heat treatment in real-time;
  - generate in real-time signals indicative of the status of the heat treatment and the temporal evolution of the quantitative indicators in the three regions; and
  - exclude the pixels whose measured temperature variation is not usable or reliable.

2. The assembly of claim 1, further comprising a second image acquisition device configured to generate at least one anatomical image.

3. The assembly of claim 2, wherein the planning unit further comprises an anatomical image processing means configured to define the three regions on the anatomical image, and a recalibration means configured to spatially match the anatomical image with the MRI anatomical image from the MRI image acquisition device.

4. The assembly of claim 1, wherein the means for calculating a reliability indicator is configured to:

- determine an uncertainty of the temperature measured in each of the three regions from a temperature variance determined over a series of temperature images; and
- determine a number of pixels in each of the three regions meeting the predefined acceptable temperature measurement uncertainty, the number corresponding to the reliability indicator of the temperature variation indicated on the temperature image.

5. The assembly of claim 1, wherein the energy applicator is a laser beam applicator, a microwave applicator, a radio-frequency wave applicator, a focused ultrasound applicator, or a cryogenic energy applicator.

6. The assembly of claim 1, further comprising a display unit configured to display the quantitative indicators of the status of the treatment in each of the three regions.

7. An assembly for heat treatment of a target region of a biological tissue comprising:

- a thermal energy generator;
- an energy applicator coupled to the generator and configured to deposit thermal energy in the target region so as to induce a temperature variation;
- a magnetic resonance imaging (MRI) image acquisition device configured to generate at least one MRI anatomical image and at least one MRI phase image;
- a planning unit comprising an MRI image processing means configured to define three regions including the target region, a region to be preserved, and a neutral region on the at least one MRI anatomical image, the MRI image processing means being configured to assign a heat treatment setpoint to each of the three regions and an acceptable temperature measurement uncertainty to each of the three regions;

a unit for monitoring evolution of the status of the heat treatment and configured to receive data from the planning unit and data from the MRI image acquisition device in real-time during a heat treatment phase, the monitoring unit comprising a means for generating temperature images from the at least one MRI phase image, means for calculating a reliability indicator of the temperature variation indicated on the temperature image, and a means for calculating a quantitative indicator of the status of the heat treatment in each of the three regions;

wherein the means for calculating a quantitative indicator of the status of the heat treatment is configured to:

spatially match the MRI anatomical image with the temperature images generated during the heat treatment;

compare the temperature and/or a thermal dose associated with each pixel of the three regions with the predefined heat treatment setpoint in each of the three regions;

determine the number of pixels that meet the predefined heat treatment setpoint for each of the three regions, the number corresponding to the quantitative indicator of the status of the heat treatment in real-time;

generate in real-time signals indicative of the status of the heat treatment and the temporal evolution of the quantitative indicators in the three regions;

wherein the heat treatment setpoint assigned to the target region corresponds to a minimum temperature to be reached, a minimum thermal dose to be reached, or a curve of the evolution of the temperature over the predefined time.

8. The assembly of claim 7, further comprising a second image acquisition device configured to generate at least one anatomical image.

9. The assembly of claim 8, wherein the planning unit further comprises an anatomical image processing means configured to define the three regions on the anatomical image, and a recalibration means configured to spatially match the anatomical image with the MRI anatomical image from the MRI image acquisition device.

10. The assembly of claim 7, wherein the means for calculating a reliability indicator is configured to:

determine an uncertainty of the temperature measured in each of the three regions from a temperature variance determined over a series of temperature images; and determine a number of pixels in each of the three regions meeting the predefined acceptable temperature measurement uncertainty, the number corresponding to the reliability indicator of the temperature variation indicated on the temperature image.

11. An assembly for heat treatment of a target region of a biological tissue comprising:

a thermal energy generator;

an energy applicator coupled to the generator and configured to deposit thermal energy in the target region so as to induce a temperature variation;

a magnetic resonance imaging (MRI) image acquisition device configured to generate at least one MRI anatomical image and at least one MRI phase image;

a planning unit comprising an MRI image processing means configured to define three regions including the target region, a region to be preserved, and a neutral region on the at least one MRI anatomical image, the MRI image processing means being configured to assign a heat treatment setpoint to each of the three regions and an acceptable temperature measurement uncertainty to each of the three regions;

a unit for monitoring evolution of the status of the heat treatment and configured to receive data from the planning unit and data from the MRI image acquisition device in real-time during a heat treatment phase, the monitoring unit comprising a means for generating temperature images from the at least one MRI phase image, means for calculating a reliability indicator of the temperature variation indicated on the temperature image, and a means for calculating a quantitative indicator of the status of the heat treatment in each of the three regions;

wherein the means for calculating a quantitative indicator of the status of the heat treatment is configured to:

spatially match the MRI anatomical image with the temperature images generated during the heat treatment;

compare the temperature and/or a thermal dose associated with each pixel of the three regions with the predefined heat treatment setpoint in each of the three regions;

determine the number of pixels that meet the predefined heat treatment setpoint for each of the three regions, the number corresponding to the quantitative indicator of the status of the heat treatment in real-time;

generate in real-time signals indicative of the status of the heat treatment and the temporal evolution of the quantitative indicators in the three regions;

wherein the heat treatment setpoint assigned to the region to be preserved corresponds to a maximum temperature not to be exceeded or a maximum thermal dose not to be exceeded.

12. The assembly of claim 11, further comprising a second image acquisition device configured to generate at least one anatomical image.

13. The assembly of claim 12, wherein the planning unit further comprises an anatomical image processing means configured to define the three regions on the anatomical image, and a recalibration means configured to spatially match the anatomical image with the MRI anatomical image from the MRI image acquisition device.

14. The assembly of claim 11, wherein the means for calculating a reliability indicator is configured to:

determine an uncertainty of the temperature measured in each of the three regions from a temperature variance determined over a series of temperature images; and determine a number of pixels in each of the three regions meeting the predefined acceptable temperature measurement uncertainty, the number corresponding to the reliability indicator of the temperature variation indicated on the temperature image.

15. An assembly for heat treatment of a target region of a biological tissue comprising:

a thermal energy generator;

an energy applicator coupled to the generator and configured to deposit thermal energy in the target region so as to induce a temperature variation;

a magnetic resonance imaging (MRI) image acquisition device configured to generate at least one MRI anatomical image and at least one MRI phase image;

a planning unit comprising an MRI image processing means configured to define three regions including the target region, a region to be preserved, and a neutral region on the at least one MRI anatomical image, the MRI image processing means being configured to assign a heat treatment setpoint to each of the three regions and an acceptable temperature measurement uncertainty to each of the three regions;

a unit for monitoring evolution of the status of the heat treatment and configured to receive data from the planning unit and data from the MRI image acquisition device in real-time during a heat treatment phase, the monitoring unit comprising a means for generating temperature images from the at least one MRI phase image, means for calculating a reliability indicator of the temperature variation indicated on the temperature image, and a means for calculating a quantitative indicator of the status of the heat treatment in each of the three regions;

wherein the means for calculating a quantitative indicator of the status of the heat treatment is configured to:

spatially match the MRI anatomical image with the temperature images generated during the heat treatment;

compare the temperature and/or a thermal dose associated with each pixel of the three regions with the predefined heat treatment setpoint in each of the three regions;

determine the number of pixels that meet the predefined heat treatment setpoint for each of the three regions, the number corresponding to the quantitative indicator of the status of the heat treatment in real-time;

generate in real-time signals indicative of the status of the heat treatment and the temporal evolution of the quantitative indicators in the three regions;

wherein the heat treatment setpoint assigned to the neutral region corresponds to a maximum temperature not to be exceeded or a maximum thermal dose not to be exceeded.

16. The assembly of claim 15, further comprising a second image acquisition device configured to generate at least one anatomical image.

17. The assembly of claim 16, wherein the planning unit further comprises an anatomical image processing means configured to define the three regions on the anatomical image, and a recalibration means configured to spatially match the anatomical image with the MRI anatomical image from the MRI image acquisition device.

18. The assembly of claim 15, wherein the means for calculating a reliability indicator is configured to:

determine an uncertainty of the temperature measured in each of the three regions from a temperature variance determined over a series of temperature images; and determine a number of pixels in each of the three regions meeting the predefined acceptable temperature measurement uncertainty, the number corresponding to the reliability indicator of the temperature variation indicated on the temperature image.

19. A method for real-time quantitative monitoring of a status of a heat treatment of a biological tissue, the method comprising:

generating at least one MRI anatomical image;

defining three regions including a target region, a region to be preserved, and a neutral region on the MRI anatomical image;

determining a first set of target pixels within the target region, a second set of pixels to be preserved within the region to be preserved, and a third set of neutral pixels within the neutral region;

assigning a heat treatment setpoint to each of the pixels in the three regions;

assigning an acceptable temperature measurement uncertainty to each of the pixels in the three regions;

determining the reliability indicator of the temperature variation indicated on a temperature image, the reliability indicator corresponding to the number of pixels meeting the predefined acceptable temperature measurement uncertainty in the three regions;

generating temperature images from the phase images transmitted by the MRI image acquisition device;

calculating the quantitative indicator of the status of the heat treatment, the indicator corresponding to the number of pixels or the percentage of pixels that meet the predefined heat treatment setpoint for each of the three regions;

excluding the pixels whose measured temperature variation is not usable or reliable; and displaying in real-time a 3D temperature map and a 3D thermal dose map, the quantitative indicator of the status of the heat treatment in each of the three regions.

20. The method of claim 19, further comprising a planning phase carried out before the heat pretreatment phase, the planning phase comprising:

generating at least one anatomical image;

defining the target region, the region to be preserved, and the neutral region on the anatomical image;

determining a first set of target pixels within the target region, a second set of pixels to be preserved within the region to be preserved, and a third set of neutral pixels within the neutral region;

and wherein the pretreatment phase further comprises a recalibration between the anatomical image and the MRI anatomical image to define the three regions on the MRI anatomical image.

21. The method of claim 19, wherein the displaying comprises generating a visual and/or audible indicator indicating that the heat treatment is completed in the target region when the number of pixels of the target region meeting the treatment setpoint reaches a predefined threshold.

22. The method of claim 19, wherein the displaying comprises generating a visual and/or audible indicator indicating that the safety setpoint in the region to be preserved is not in compliance when the number of pixels of the region to be preserved not meeting the predefined setpoint is greater than a predefined threshold.

* * * * *